United States Patent [19]

Cowen

[11] Patent Number: 5,067,485
[45] Date of Patent: Nov. 26, 1991

[54] CORPUS CAVERNOSUM IMPLANT DEVICE

[75] Inventor: Timothy B. Cowen, Andover, Minn.

[73] Assignee: Mentor Corporation, Minneapolis, Minn.

[21] Appl. No.: 522,821

[22] Filed: May 14, 1990

[51] Int. Cl.⁵ .......................... A61F 5/00; A61F 2/04
[52] U.S. Cl. ............................................ 128/79; 623/12
[58] Field of Search ................. 623/12, 26; 128/79 A, 128/843

[56] References Cited

U.S. PATENT DOCUMENTS

| | | | |
|---|---|---|---|
| 4,187,839 | 2/1980 | Nuwayser et al. | 128/79 |
| 4,353,360 | 10/1982 | Finney et al. | 128/79 |
| 4,392,562 | 7/1983 | Burton et al. | 128/79 |
| 4,628,912 | 12/1986 | Fischell | 128/79 |
| 4,665,902 | 5/1987 | Goff et al. | 128/79 |
| 4,730,607 | 3/1988 | Fischell | 128/79 |
| 4,790,298 | 12/1988 | Trick | 128/79 |
| 4,807,608 | 2/1989 | Levius | 128/79 |

Primary Examiner—David J. Isabella
Assistant Examiner—Elizabeth M. Burke
Attorney, Agent, or Firm—Hugh D. Jaeger

[57] ABSTRACT

A technique for the treatment of male impotence. The apparatus to be implanted in the corpus cavernosum of the penis is a cylinder of an implantable polymer. The cylinder is generally flexible and has a plurality of transitions from a lesser diameter to a greater diameter. As the cylinder is filled with fluid under pressure, the areas of lesser diameter tend to expand, thereby effectively lengthening the cylinder without an unacceptable increase in girth. Optional rings may be positioned over the areas of lesser diameter to prevent collapse. An optional outer sheath also improves longitudinal stability.

5 Claims, 9 Drawing Sheets

CORPUS CAVERNOSUM IMPLANT DEVICE

CROSS REFERENCES TO CO-PENDING APPLICATIONS

None.

BACKGROUND OF THE INVENTION

1. Field of the Invention

This invention relates to an implantable medical device, and more particularly, to a prosthesis assembly for the remedy of impotence.

2. Description of the Prior Art

Inflatable or distensible penile implants have been used for treatment of impotence. An early patent on an implant system for this purpose is U.S. Pat. No. 4,009,711, issued to Uson, et al., which discloses a pair of inflatable tubes to be surgically implanted in a corpus cavernosum of the penis. Each of the tubes includes a non-distensible portion of a semi-rigid material to be implanted into the root end of the corpus cavernosum and a pendulous, distensible body portion. The distensible or inflatable body or tube is connected by tubing to a fluid reservoir located in the scrotal sac, and a check valve is provided to control the flow of fluid between the reservoir and inflatable tube. A similar device is disclosed in U.S. Pat. No. 4,235,227, issued to Yamanaka.

A more recent patent on the prosthesis is U.S. Pat. No. 4,726,360, which discloses that each extendable tube can be encased in an outer sleeve which is permanently filled with a fluid, thereby providing an outer, annular pressure chamber.

The distensible tubes in the implants, which have heretofore been used, are formed of silicone and have limited elasticity to avoid girth expansion of the tubes. The limited elasticity of the tubes, however, undesirably limits their axial extendability.

U.S. Pat. No. 4,730,607, issued to Fischell discloses that the axial extendibility of a stiffener cylinder can be improved by providing several bellow-type folds in the tube. The bellow folds are described as having sufficient depth to increase the extendibility of the tube from 6 percent to about 13 percent. Fischell teaches that these folds should preferably be located near the base to function as a strain relief. However, the extendibility is unsatisfactorily limited if the stiffener cylinder is supplied with an outer sheath.

Despite the various attempts to provide a satisfactory penile implant, none of the prior art approaches has provided a corpus cavernosum implant which is extendable for a significant percentage of its length without an objectionable increase in girth. In such structure it is important to minimize the pressure or stress points of the tube under inflation to avoid premature failure.

While the bellows configuration of an inflatable tube is an apparent solution to the necessity for optimum elongation of the tube, this structure has not found acceptance in practice, presumably because of the sharp folds and edges of a bellows construction which localizes stress at the folds, thus limiting the practicality of this approach. This approach also has some aesthetic disadvantages in tactile sensing of the irregular shape.

SUMMARY OF THE INVENTION

This invention comprises a penile implant system utilizing a corpus cavernosum implant device having an inflatable cylinder formed with a flexible wall of an implantable polymer and having an axial cross section of alternating diameters along a major portion of its length. Preferably, the inflatable cylinder is used with rings positioned along the outer surface to control expansion girth, improve longitudinal stability when inflated, and enhance the aesthetics. An optional outer sheath and the annular space between the distensible cylinder may be filled with a body compatible fluid such as a saline solution or gel. The penile implant system preferably uses a pair of the inflatable cylinders which are implanted in the corpus cavernosum of the penis. The cylinders are connected with tubing to a reservoir and pump with check valves to permit inflation of the cylinders.

It is an objective of this invention to provide a corpus cavernosum implant having improved extendibility without excessive girth expansion.

It is a further object of this invention to provide a system utilizing a corpus cavernosum inflatable cylinder implant of improved elongation characteristics.

It is also an object of this invention to provide an inflatable cylinder for use as a corpus cavernosum implant having a high degree of elongation with minimal pressure points.

It is an additional object of this invention to provide an inflatable cylinder for use as a corpus cavernosum implant of improved extendibility and improved longevity.

Other and related objects will be apparent from the following description of the invention.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 2 is a cutaway view of the inflatable inner cylinder used in the invention;

DESCRIPTION OF THE PREFERRED EMBODIMENTS

Figure 1:
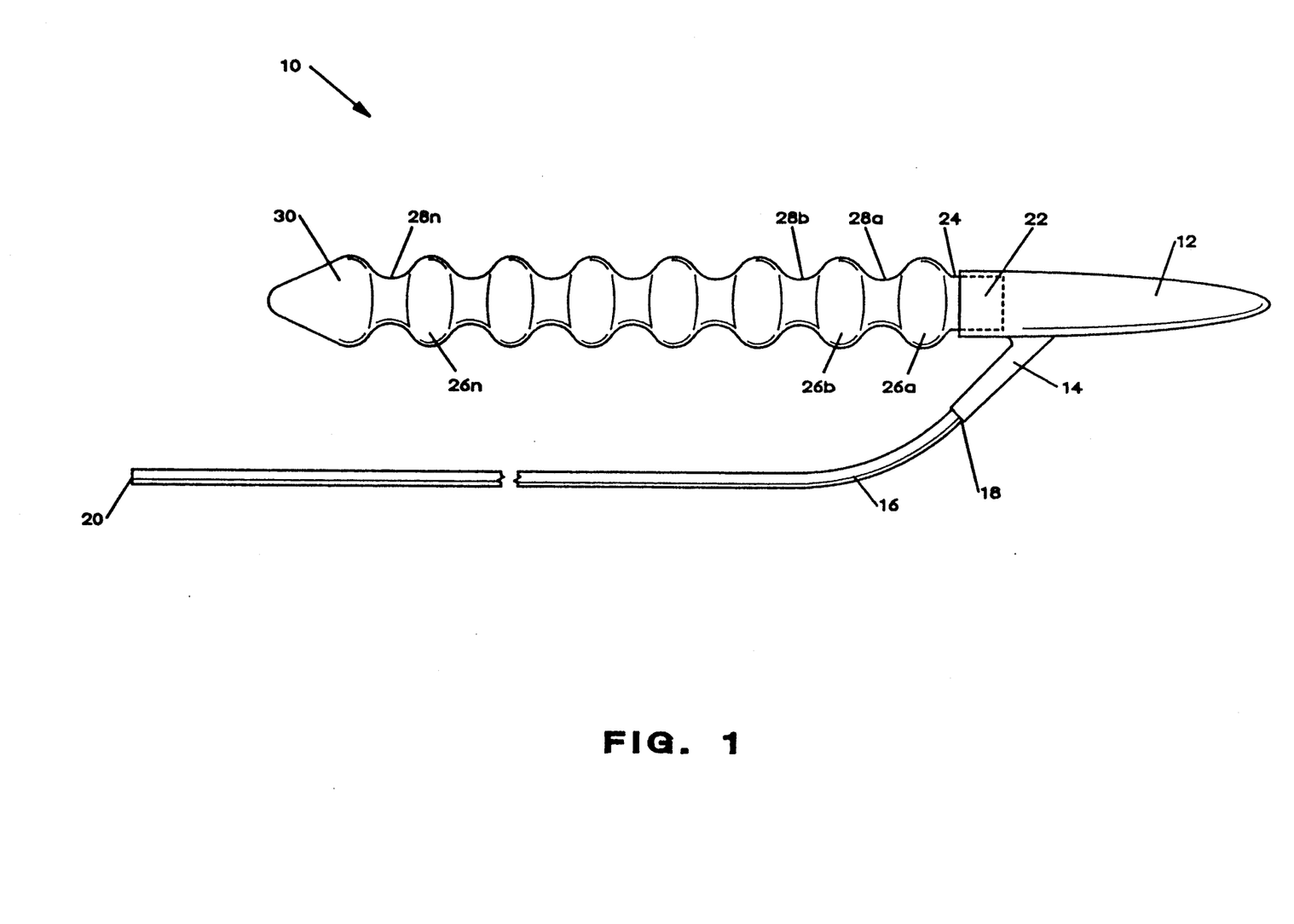
FIG. 1 is a plan view of the inflatable inner cylinder of the invention.

FIG. 1 is a plan view of the inner cylinder 10 of the present invention coupled to base mount 12 and fluid access tube 16. Inner cylinder 10 may be directly implanted in this configuration for maximum extendibility and minimum rigidity in the flaccid state or may be used as the inner member of a structure in accordance with the teachings below.

Inner cylinder 10 is preferably fabricated as single hollow cylinder from an implantable polymer such as polyurethane. Distal tip 30 is conically shaped and closed to permit maintenance of induced pressure in the erect state. Proximal end 22 of inner cylinder 10 is open. It is slipped into the distal end of semi-rigid base unit 12 and sealed using an adhesive or other permanent sealing technique.

The main body of inner cylinder 10 is characterized by a number of corrugations as shown. In the preferred embodiment these corrugations produce a sinusoidal outer dimension as shown. Other shapes may be used. However, each maximum diameter 26a-26n and each minimum diameter 28a-28n should present a smoothly curved surface. This feature is important to ensure that maximum extendibility is achieved in the erect state with a desirable change in girth from the flaccid state. The smooth curves also are important to the tactile and visual aesthetics whenever the major portion of the inner cylinder 10 is corrugated.

Fluid access port 14 of base member 12 is coupled to flexible fluid access tube 16 as shown. A fluid pump (not shown) is coupled to the proximal end 20 of flexible fluid access tube 16. In this manner, fluid may be pumped into or evacuated from inner cylinder 10. By using an essentially non-compressible fluid, inner cylinder 10 is extended and stiffened when the fluid is pumped into inner cylinder 10 and is shortened and relaxed when fluid is pumped out. Because of the smooth corrugations of inner cylinder 10 (i.e. maximum diameters 26a-26n and 28a-28n), inner cylinder 10 is readily extendible without a significant change in girth.

FIG. 2 is a cross-sectional view of the structure of FIG. 1 wherein all references are as previously described. Note that fluid communication between fluid access port 14 and inner cylinder 10 is achieved through fluid channel 32 of base mount 12.

Figure 3:
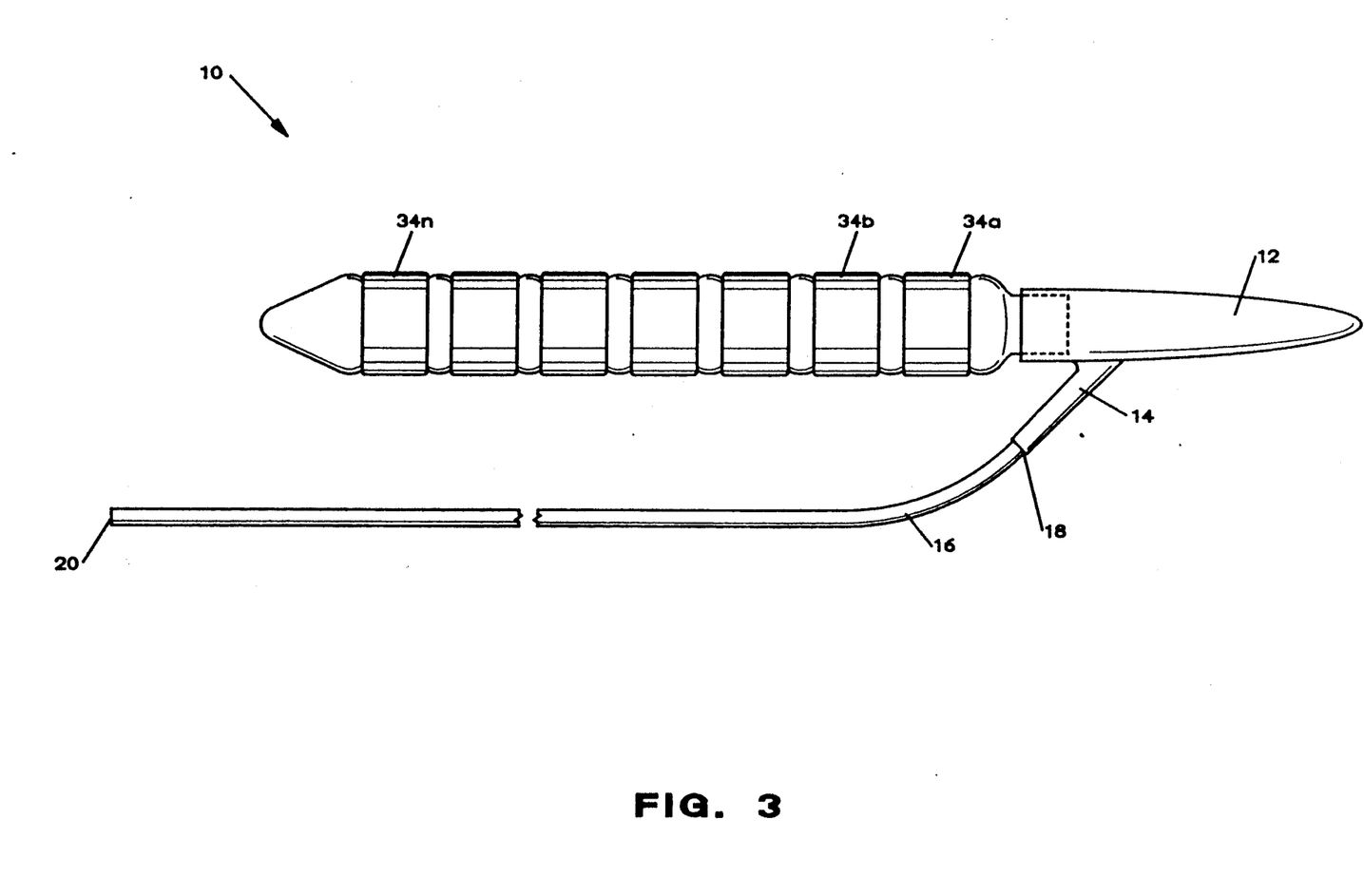
FIG. 3 is a plan view of the inflatable inner cylinder with rings.

FIG. 3 is a plan view of inner cylinder 10 having rings 34a-34n applied to the outside of minimum diameters 28a-28n, respectively. Rings 34a-34n are fabricated from an implantable polymer which is not rigid. The inner diameter of rings 34a-34n is chosen to fit snugly over minimum diameters 28a-28n, respectively.

The primary function of rings 34a-34n is to provide longitudinal rigidity in the erect state. That is rings 34a-34n tend to prevent inner cylinder 10 from collapsing about one of the minimum diameters 28a-28n upon the application of force from proximal to distal ends of inner cylinder 10 during use.

To make the implanted prosthesis more presentable both tactilely and visually, the outer diameter of rings 34a-34n should be the same as the outer diameter of maximum diameters 26a-26n. To prevent longitudinal movement of rings 34a-34n during successive inflations and deflations of inner cylinder 10, rings 34a-34n may be adhesively attached to minimum diameters 26a-26n, respectively.

The use of rings to prevent collapse of inner cylinder 10 in the inflated state causes inner cylinder 10 to be somewhat stiffer in the deflated state. However, maintenance of constant girth from the flaccid to the erect state is somewhat improved.

Figure 4:
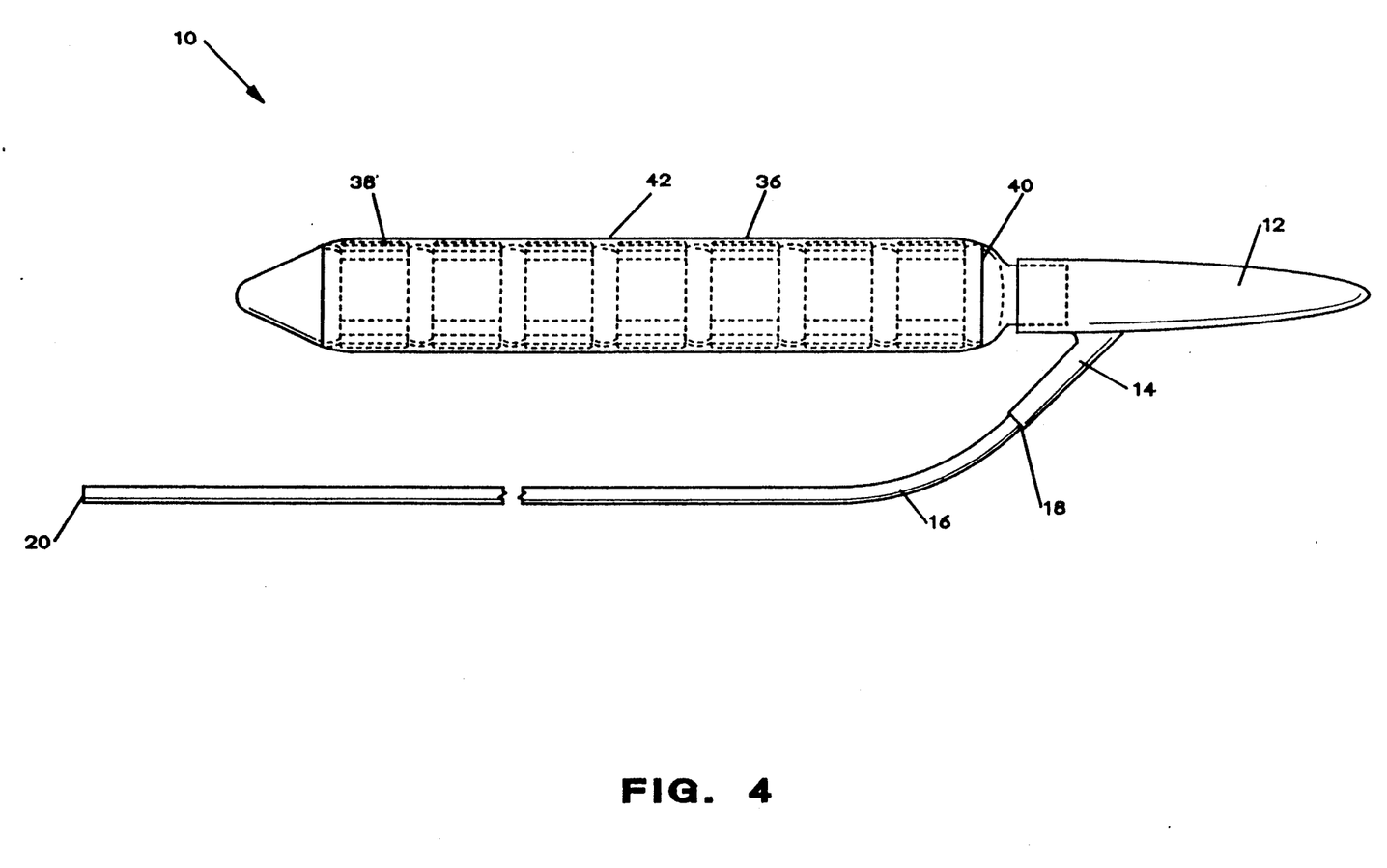
FIG. 4 is a plan view of the inflatable inner cylinder with rings covered by an outer sheath.

FIG. 4 is a plan view of the structure of FIG. 3 employing an outer sheath 36 to prevent movement of rings 34a-34n. Again aesthetics and girth control are improved at the expense of increased stiffness in the flaccid state.

In this configuration, the outer surface of the implant appears to be completely cylindrical without the variations in cross-sectional diameter found in inner cylinder 10. By sealingly attaching the distal end 38 and proximal end 40 of outer sheath 36 to inner cylinder 10, interference by fibrotic growth with the operation of the rings during inflation and deflation is minimized.

Figure 5:
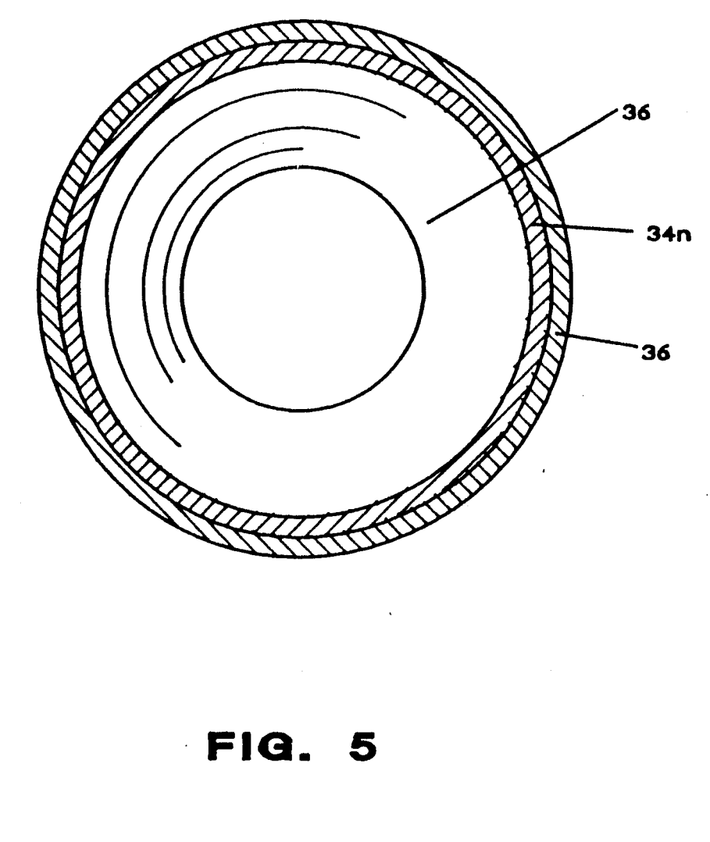
FIG. 5 is a cross-sectional view of the structure of FIG. 4.

FIG. 5 is a cross sectional view of the structure of FIG. 4. All references are as previously described.

Figure 6:
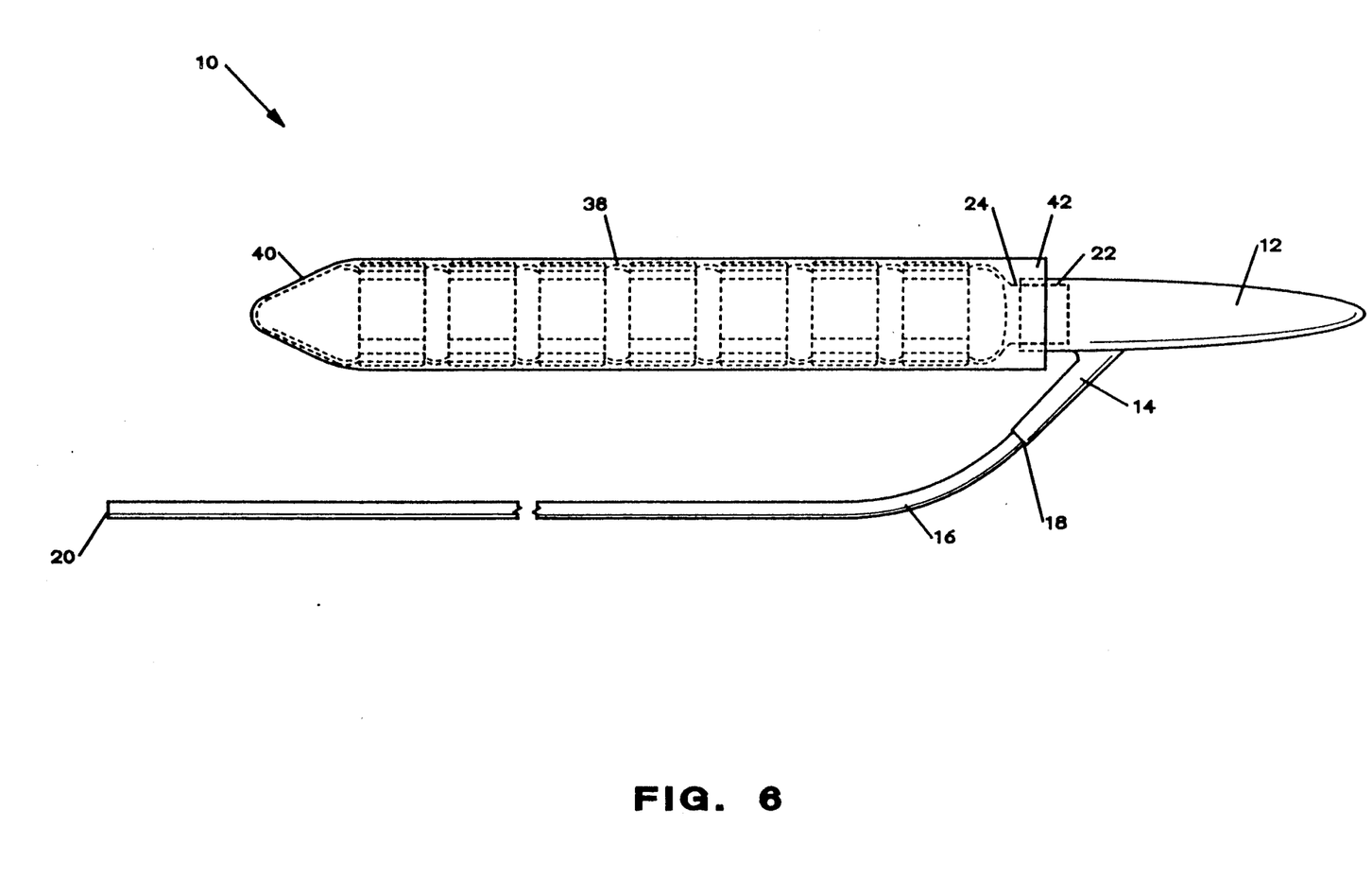
FIG. 6 is a plan view of an alternative embodiment.

FIG. 6 is a plan view of an alternative embodiment of the present invention. In this mode, an outer sheath 38 covers all of inner cylinder 10 including distal tip 30. Therefore, the distal end of outer sheath 38 need not be attached to inner cylinder 10. The proximal end of outer sheath 38 is sealingly attached to inner cylinder 10 or base mount 12 at 42. This permits the space between inner cylinder 10 and outer sheath 38 to be filled with a fluid such as sterile saline. The resulting structure is yet more resistant to collapse under longitudinal force but stiffer in the deflated (flaccid) state.

Figure 7:
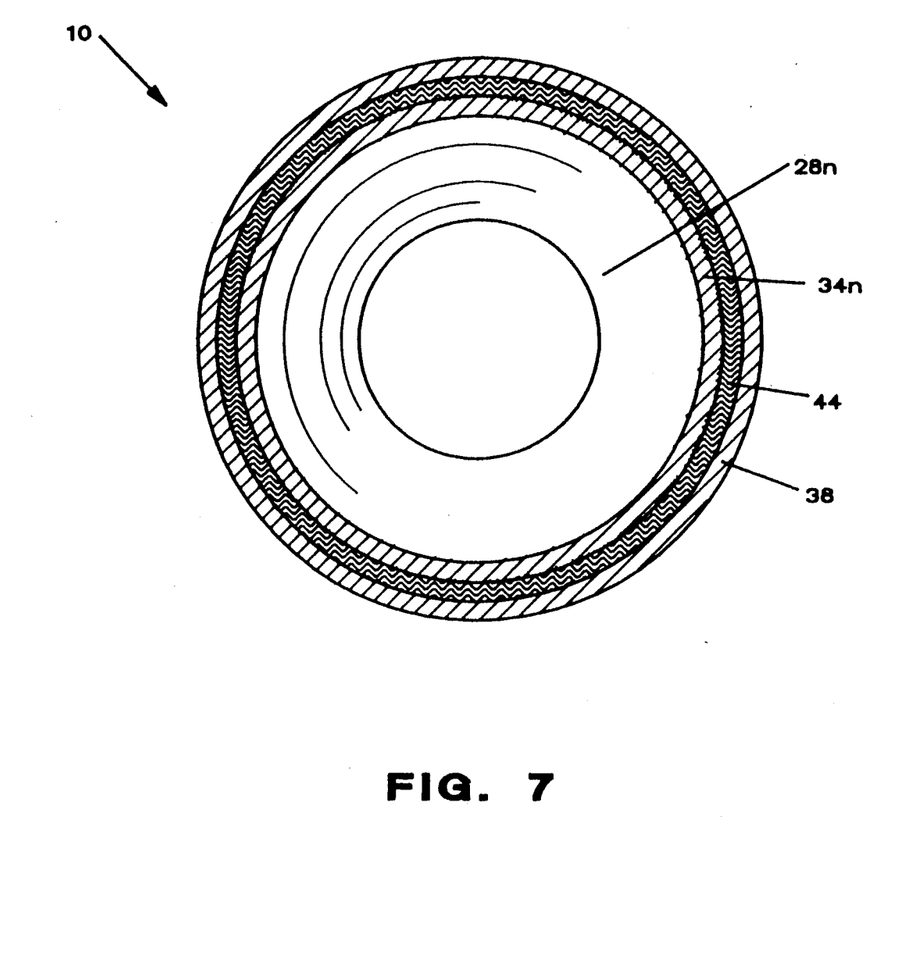
FIG. 7 is a cross-sectional view of the structure of FIG. 6.

FIG. 7 is a cross-sectional view of the structure of FIG. 6. Note that sterile saline 44 fills the space between the inner diameter of outer sheath 38 and the outer diameter of ring 34n.

Figure 8:
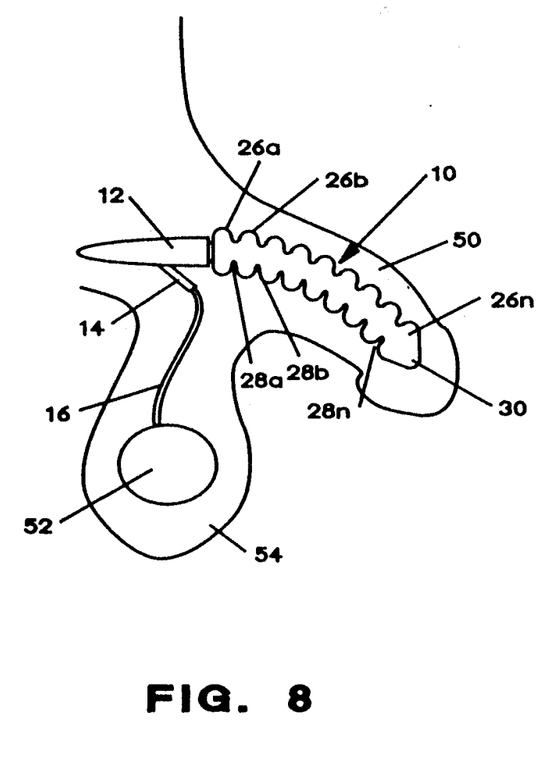
FIG. 8 is a schematic view of the system in a flaccid state.

FIG. 8 is a schematic diagram of the present invention as implanted in a patient. Inner cylinder 10 is shown in the deflated or flaccid state. Fluid reservoir pump 52 may be implanted in scrotum 54, as shown.

Figure 9:
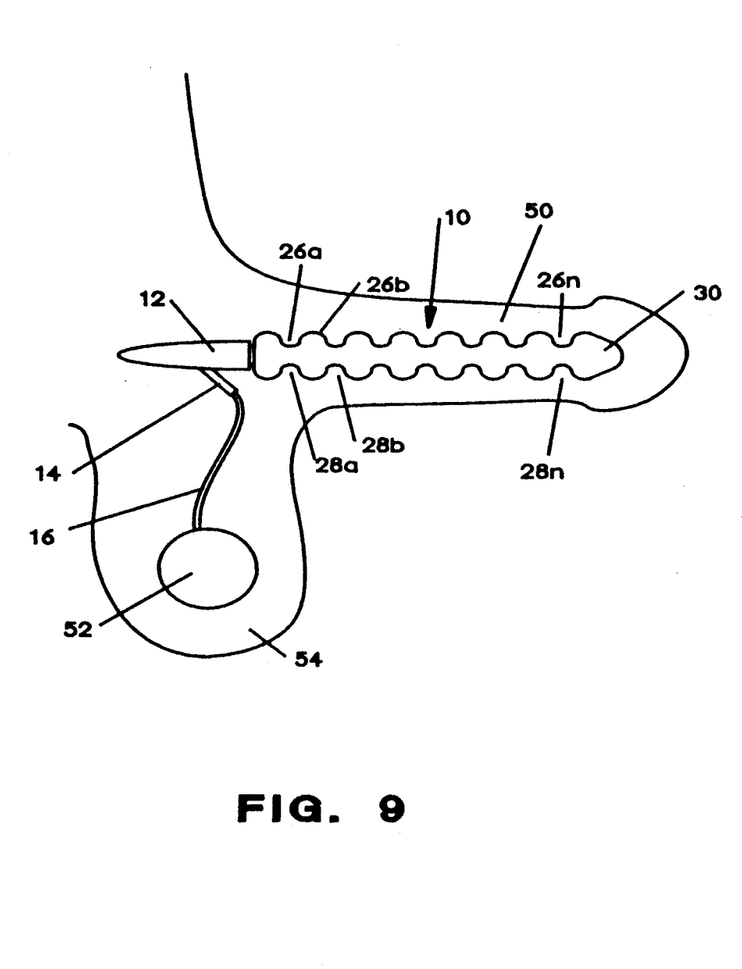
FIG. 9 is a schematic view of the system in an erect state.

FIG. 9 is a schematic diagram of the present invention of FIG. 8 shown in the inflated (erect) state.

The invention has been described with reference to the illustrated and presently preferred embodiments. It is not intended that the invention be unduly limited by this disclosure of the presently preferred embodiments. Instead, it is intended that the invention be defined, by the means, and their equivalents set forth in the following claims.

I claim:

1. An implantable penile prosthesis comprising:
   a. a hollow inner cylinder of a flexible biocompatible material having an outer surface forming a plurality of smooth sinusoidal transitions from a minimum diameter to a maximum diameter in both a flaccid and a pressurized state, said plurality of sinusoidal transitions occupying a majority of the outer surface area of said inner cylinder;
   b. a base mount sealingly attached to one end of said inner cylinder;
   c. a source of pressurized fluid in fluid communication with said inner cylinder for pressurizing said inner cylinder; and
   d. at least one ring member configured for attaching to said minimum diameter of at least one of said plurality of smooth sinusoidal transitions.

2. The implantable penile prosthesis according to claim 1 wherein said at least one ring is snugly disposed over said at least one of said minimum diameters.

3. The implantable penile prosthesis according to claim 1 wherein said ring is attached by adhesive means.

4. An implantable penile prosthesis comprising: a. a hollow inner cylinder of a flexible biocompatible material which defines an inner fluid containing chamber, said inner cylinder having an outer surface forming a plurality of smooth transitions from a minimum diameter to a maximum diameter in both a flaccid and a pressurized state, said plurality of smooth transitions occupying the majority of the surface area of said inner cylinder;

b. a base mount sealingly attached to one end of said inner cylinder;
c. a source of pressurized fluid in fluid communication with
c. a source of pressurized fluid in fluid communication with said inner chamber of said inner cylinder for pressurizing said inner cylinder; and
d. an outer sheath disposed over said inner cylinder defining an outer chamber which is isolated from said inner chamber.

5. The implantable penile prosthesis according to claim 4 wherein said plurality of smooth transitions is sinusoidal.

* * * * *

UNITED STATES PATENT AND TRADEMARK OFFICE
CERTIFICATE OF CORRECTION

PATENT NO. : 5,067,485
DATED : Nov. 26, 1991
INVENTOR(S) : Cowen

It is certified that error appears in the above-indentified patent and that said Letters Patent is hereby corrected as shown below:

Sheet 2 of 9, insert (the reading) --FIG. 2--

Signed and Sealed this

Tenth Day of August, 1993

Attest:

MICHAEL K. KIRK

Attesting Officer     Acting Commissioner of Patents and Trademarks